United States Patent [19]

Bollag

[11] Patent Number: 4,464,394
[45] Date of Patent: Aug. 7, 1984

[54] COMPOSITIONS AND METHODS FOR USING 13-CIS VITAMIN A ACID COMPOUNDS

[75] Inventor: Werner Bollag, Basel, Switzerland

[73] Assignee: Hoffmann LaRoche Inc., Nutley, N.J.

[21] Appl. No.: 283,585

[22] Filed: Jul. 15, 1981

Related U.S. Application Data

[63] Continuation of Ser. No. 161,200, Jun. 19, 1980, abandoned, which is a continuation of Ser. No. 950,760, Oct. 12, 1978, abandoned, which is a continuation of Ser. No. 820,280, Jul. 29, 1977, abandoned, which is a continuation of Ser. No. 676,078, Apr. 12, 1976, abandoned, which is a continuation of Ser. No. 535,602, Dec. 23, 1974, abandoned, which is a continuation of Ser. No. 384,848, Aug. 2, 1976, abandoned, which is a continuation-in-part of Ser. No. 49,976, Jun. 25, 1970, abandoned.

[30] Foreign Application Priority Data

Jun. 23, 1970 [CH] Switzerland .......................... 9474/70

[51] Int. Cl.³ ............................................. A61K 31/19
[52] U.S. Cl. ..................................................... 424/317
[58] Field of Search ......................................... 424/317

[56] References Cited

U.S. PATENT DOCUMENTS

3,252,865  5/1966  Klavi ................................... 424/344

OTHER PUBLICATIONS

Prutkin, J. of Investigative Dermatology, vol. 49, No. 2, pp. 165–172, Aug. 1967.
Chemical Abstracts, 59:7918d, (1963).
Zile et al., Biophys. Acta, 141, (1967), pp. 639–641.
Chemical Abstracts (I), 68:28185(S), 1968.
Stuttgen, Dermatologica, 124:78–79, (1962).
Oroshnik, J. Am. Chem. Soc., 74, pp. 295–304, (1952).
Planta et al., Helv. Chim. Acta, vol. 45, pp. 548–561.
DeMan et al., Netherland J. of Agricultural Science, vol. 6, pp. 237–244, (1958).
DeMan et al., Nature, 201, pp. 77–78, (1964).
Murray, Proc. Soc. Exp. Biol. Med., vol. 111, pp. 609–611, (1962).

*Primary Examiner*—Jerome D. Goldberg
*Attorney, Agent, or Firm*—Jon S. Saxe; William H. Epstein; Bernard S. Leun

[57] ABSTRACT

Methods for the prophylaxis of certain premalignant conditions and epithelial carcinomas comprising systemically administrating 13-cis vitamin A acid and a suitable pharmaceutical carrier material are described and compositions containing 13-cis Vitamin A acid suitable for systemic administration are disclosed.

13 Claims, No Drawings

COMPOSITIONS AND METHODS FOR USING 13-CIS VITAMIN A ACID COMPOUNDS

RELATED APPLICATIONS

This application is a continuation of application Ser. No. 161,200 filed June 19, 1980, which in turn is a continuation of Ser. No. 950,760 filed Oct. 12, 1978, now abandoned, which in turn is a continuation application of Ser. No. 820,280 filed July 29, 1977, now abandoned, which in turn is a continuation of Ser. No. 676,078 filed Apr. 12, 1976, now abandoned, which in turn is a continuation of Ser. No. 535,602 filed Dec. 23, 1974, now abandoned, which in turn is a continuation of Ser. No. 384,848 filed Aug. 2, 1973, now abandoned, which in turn is a continuation-in-part of U.S. patent application Ser. No. 49,976 filed June 25, 1970, now abandoned.

BACKGROUND OF THE INVENTION

Vitamin A compounds have heretofore been clinically tested in certain selected areas of dermatology. For example, a large number of dermatologists have experimentally treated certain diseases such as, for example, ichthyosis, Darier's disease, psoriasis and other keratoses by the topical administration of vitamin A. In addition, some keratoses such as, for example, ichthyosis vulgaris and ichthyosiform erythrodermia have been experimentally treated by the systemic administration of vitamin A.

Inconsistent results obtained with vitamin A palmitate utilized both locally and systemically has caused some workers, notably Stuttgen, to experiment with attempts to influence keratoses locally with vitamin A acid. He reported in Dermatologica 124: 65–80 (1962) that positive results were obtained with ichthyosis vulgaris, ichthyosiform, erythrodermia and also with three cases of senile keratoses. More recently, other workers have realized therapeutic success with locally applied vitamin A acid in treating lamellar ichthyosis, psoriasis and epidermolytic hyperkeratoses. It has now been discovered that 13-cis vitamin A acid or a pharmaceutically acceptable salt thereof is particularly effective systemically in the prophylaxis of certain epithelia carcinomas and premalignant conditions of the epithelial cells.

The epithelium forms the outer protecting surface of the body and all glands, furnishes important parts of the sense organs and lines the walls of the internal cavities. It is best classified in terms of the shape of the epithelial cells and their arrangement in epithelial sheets. Although the cells may vary in shape with movement of the epithelium, they are mainly flat, i.e. squamous cells, cuboidal, or columnar in appearance. Sheets of these cells are variously classified as simple where a single layer of cells exists or stratified where many layers exist. Epithelial cells may have on their free surface motile, hairlike processes called cilia or smaller, non-motile processes constituting a brush border and can be cornified or not. The epithelial cells perform an extremely important function in the process of metabolism in that all substances absorbed from the outside medium and eliminated to the outside medium must pass through them. The present invention is directed to cancers affecting these vital cells.

SUMMARY OF THE INVENTION

In accordance with the present invention, a prophylaxis against certain premalignant conditions and epithelial carcinomas is afforded through the systemic administration of an effective amount of 13-cis vitamin A acid, or the equivalent amount of a pharmaceutically acceptable salt thereof as well as pharmaceutical compositions for systemic administration containing 13-cis vitamin A acid or its pharmaceutically acceptable salt are provided.

DETAILED DESCRIPTION OF THE INVENTION

In accordance with the present invention, 13-cis vitamin A acid is systemically administered to persons susceptible to certain epithelial carcinomas of the skin, gastrointestinal, respiratory or genito-urinary tract. Certain of the epithelial carcinomas to be prevented in accordance with the present invention frequently pass through a definite premalignant stage which can be diagnosed as such. It is a statistical fact that 20 to 30% of such premalignant conditions develop into epithelial carcinomas. Each such premalignant condition, however, has a propensity to mature into an epithelial carcinoma if allowed to remain untreated. In these instances, the premalignant stage may be treated systemically to prevent development of an epithelial carcinoma therefrom. In other instances, even though a definite premalignant condition cannot be positively diagnosed, the individual who may be susceptible to the epithelial carcinomas is maintained on a regimen of the compositions which according to the present invention contain as the active ingredient 13-cis vitamin A acid.

As utilized herein, the expression "an individual who may be susceptible to epithelial carcinomas" may be defined as a person who is subjected to exposure to carcinogenic irritants or conditions such as, for example, the inhalation of tobacco smoke or hydrocarbon fumes, exposure to excess sunlight, radioactive material, chemical fumes and the like. A specific example of an individual who may be susceptible to epithelial carcinoma are uranium miners who are subjected to radioactive material and have known premalignant bronchogenic disease. It is recognized in medicine that such miners whose sputum cytology is positive in terms of these conditions will ultimately develop clinically evident lung carcinoma.

The terminology "epithelial carcinomas" utilized with regard to the prophylactic methods of the present invention encompasses carcinomas affecting epithelial cells of diverse parts of the human body, e.g. stratified squamous epithelial cells of the skin and mucous membranes, columnar epithelial cells of the intestinal tract, ciliated epithelial cells of the genitalia and parts of the respiratory tract, such as the nasal passages and pseudostratified epithelial cells of the trachea and bronchi. As recognized by the oncologist, carcinomas affecting these cells include those of the epithelium of the skin, tongue, pharynx, larynx, bronchus, esophagus, stomach, large bowel, bladder, cervix and vulva and the like.

The daily dosage of 13-cis vitamin A acid in accordance with the present invention will vary with the needs of the patient, particularly in those instances where a definite premalignant condition has been diagnosed. Generally, a daily dose by enteral or parenteral administration of from about 0.05 mg. to about 3.0 mg. per kg. of body weight of the patient is utilized. More preferably, a dosage of from about 0.1 mg. to about 1.0 mg. per kg. is utilized. This dosage may be administered in any suitable dosage schedule according to the desires of the clinician in view of the requirements of the patient, the existence of a premalignant condition of the epithelial cells and other factors such as age of the patient and the like.

In accordance with the present invention, 13-cis vitamin A acid is administered by either enteral or parenteral modes. Suitable pharmaceutical dosage forms for enteral administration include tablets, capsules, dragees, syrups, suspensions, solutions, suppositories and the like. These pharmaceutical unit dosage forms for enteral administration may suitably contain the 13-cis vitamin A acid or a pharmaceutically acceptable salt thereof in an amount of from about 5.0 mg to about 50.0 mg. Parenteral dosage forms may be infusions or injectable solutions which can be injected intravenously or intramuscularly. These preparations can contain other medicinally active substances as well as inert binding agents, fillers, carriers or diluents. Additional additives such as flavoring agents, preservatives, stabilizers, emulsifying agents, buffers and the like may be added in accordance with accepted practices of pharmaceutical compounding. It is preferred to incorporate into the preparations herein described one or a mixture of antioxidants recognized as being suitable for such preparations such as, for example, N-methyl-γ-tocopherolamine, tocopherols, butylated hydroxyanisole, butylated hydroxytoluene, ethoxyquin and the like. The carriers and diluents utilized may be organic or inorganic substances such as, for example, water, gelation, lactose, starches, magnesium stearate, talc, gum arabic, polyalkyleneglycols and the like. A preferred systemic dosage form comprising capsules of hard or soft gelatin, methylcellulose or of another suitable material easily dissolved in the digestive tract.

In the practice of the invention, the preferred pharmaceutically acceptable salts of 13-cis vitamin A acid are the alkali metal salts. Especially preferred among the alkali metal salts is the sodium salt.

Experiments have demonstrated that a dosage of 13-cis vitamin A acid between 10 mg. and 300 mg., well above the prophylactic dosages contemplated herein, administered daily per os over a period of several weeks to several months is well tolerated. This dosage corresponds to between 40,000 and about 1,200,000 international units of vitamin A activity. With doses of from 200 mg. to 300 mg., which correspond to from about 800,000 to about 1,200,000 international units of vitamin A activity, some symptoms of hypervitaminosis-A can occur. These side effects, where they do occur, manifest themselves in the form of headaches, head pressure, nausea, vomiting, vertigo and general nervousness, and generally disappear within one to three days after cessation of treatment or reduction of the daily dosage. Administration of high doses of 13-cis vitamin A acid, e.g. dosages above the upper limit of the ranges set forth herein may produce, over long term therapy, such side effects as loss of hair, anorexia, dry flaking skin, skin erruptions, irritation of the skin and mucous membranes, bone and joint pains, irritability, weight loss, liver and spleen enlargement and neurological symptoms originating from intracranial hypertension. 13-Cis vitamin A acid in contrast to vitamin A alcohol and esters such as vitamin A palmitate or acetate, are not stored in the body, e.g., in the liver. As a result of the fact that 13-cis vitamin A acid is not stored in the body, it is particularly suitable for prophylactic use over long periods of time. In addition, 13-cis vitamin A acid is particularly suitable for the prophylactic uses of the present invention because, over long term administration, patients report no incidence of nausea, vomiting, vertigo and no or only slight headaches. In contrast, these symptoms accompanied by the possible incidence of severe headache have been reported with similar dosage levels of other vitamin A acid active compounds, notably vitamin A acid.

Toxicity test carried out on the mouse and rat using a suspension of 13-cis vitamin A acid in rapeseed oil show that, in a 24-hour period, the $LD_{50}$ in the mouse is 1400 mg./kg. body weight and in the rat over 4000 mg./kg. body weight for both per os and intraperitoneal administration. Observations taken after a period of twenty days show that the $LD_{50}$ is over 900 mg./kg. intraperitoneally for both the mouse and rat.

Chronic toxicity testing of 13-cis vitamin A acid was carried out on rats initially weighing 60 to 80 grams over a period of thirteen weeks using a daily dose of 10 mg./kg. and 25 mg./kg. body weight respectively of 13-cis vitamin A acid in the form of gelatin beadlets administered as a food additive. During this test the general state of health of the rats remained good, no diarrheas were observed and the weight increase did not appreciably differ from a control group receiving no 13-cis vitamin A acid. Autopsy of sacrificed animals revealed no toxic organ injuries, no bone lesions or fractures and hematological values in the normal range. Slight dose dependent histological observations were observed in the following organ: increased number of foam cells in the lungs; hydropic changes in hepatocytes and increase in number and size of Kupffer cells in the liver; and hyperkeratosis and hypotrophy of hair follicles and glands of the skin. From this test, it is readily apparent that 13-cis vitamin A acid is well tolerated without toxic symptoms in daily doses of up to 25 mg./kg. per os. These results further support the efficacy of utilizing 13-cis vitamin A acid in the prophylactic situation over a long period of time in dosages such as herein described.

In an investigation utilizing a total of 18 dogs it was found that dosages of 20, 40 and 80 mg. 13-cis vitamin A acid per kg. of body weight were well tolerated over a period of three months. The overall disposition of all animals was good throughout the test. All animals had smooth fur, displayed normal food and water consumption and normal excreta. No mortalities occurred during the test and no important histological differences were noted between the dosed animals and a control group receiving no 13-cis vitamin A acid.

Clinical investigations conducted on patients where definite premalignant conditions of the skin or of mucous membranes had been diagnosed showed unequivocal regression of these lesions after systemic administration of from 20 mg. to 60 mg. in some instances up to 100 mg. daily of 13-cis vitamin A acid over a period from about two to about 12 weeks with only an occasional report of slight headache. As the premalignant conditions treated in these studies are but a definite step in the development of epithelial carcinomas of the skin or of mucous membranes, the prophylaxis of these epithelial carcinomas by the method of the invention is demonstrated by the clinical studies where such premalignant conditions are brought to regression. Thus the premalignant conditions which are brought to regression in a similar manner include different types of leucoplakias, metaplasias and other preliminary stages of epithelial carcinomas such as herein set forth. More particularly, the methods of the present invention afford a prophylaxis against epithelial carcinomas of the skin; gastrointestinal tract, e.g. the esophagus; oral cavity, e.g. the tongue; genitalia, e.g. the cervix and vulva. The methods of the present invention are further indicated in the prophylaxis of carcinomas of the respiratory tract e.g. larynx and bronchi.

The method of the present invention is equally applicable to the prophylaxis of epithelial carcinomas where administration of 13cis vitamin A acid is initiated routinely to persons who may be susceptible to such carcinomas, or after a condition which may be diagnosed as premalignant has been detected. The method of the present invention, therefore, additionally affords a prophylaxis against the herein described precancerous conditions. This prophylaxis of premalignant conditions, although inherent in the prophylaxis of the epithelial carcinomas resulting therefrom, is specifically mentioned herein as statistics reveal that not all premalignant conditions of the epithelial tissues mature into epithelial carcinomas if left untreated.

The following Examples are given as illustrations of the invention.

EXAMPLE 1

Dragees were prepared in accordance with the art of pharmaceutical compounding from the following ingredients:

| Ingredient | Weight/Dragee |
|---|---|
| 13-Cis Vitamin A Acid | 16.0 mg. |
| Lactose | 40.0 mg. |
| Corn Starch | 40.0 mg. |
| Talc | 3.5 mg. |
| Stearic Acid | 0.5 mg. |
| Coating Composition | 120.0 mg. |
| Total weight | 220.0 mg. |

EXAMPLE 2

Hard gelatin capsules were filled with the following composition:

| Ingredient | Weight/Capsule |
|---|---|
| 13-Cis Vitamin A Acid | 20.0 mg. |
| Talc | 8.0 mg. |
| Lactose | 152.0 mg. |
| Total Weight | 180.0 mg. |

EXAMPLE 3

Soft gelatin capsules were filled with the following composition:

| Ingredient | Weight/Capsule |
|---|---|
| 13-Cis Vitamin A Acid | 20.0 mg. |
| Wax Mixture | 51.5 mg. |
| Vegetable Oil | 103.0 mg. |
| Sequestrin[1] | 0.5 mg. |
| Total Weight | 175.0 mg. |

[1]Complexing agent: sodium salt of ethylenediaminetetraacetic acid.

EXAMPLE 4

Soft gelatin capsules were filled with the following compositions wherein an amount of the sodium salt of 13-cis vitamin A acid equivalent to 20.0 mg. of the free acid was utilized:

| Ingredient | Weight/Capsule |
|---|---|
| 13-Cis Vitamin A Acid, Sodium Salt | 21.46 mg. |
| Wax Mixture | 51.50 mg. |
| Vegetable Oil | 101.54 mg. |
| Sequestrin[1] | 0.50 mg. |
| Total Weight | 175.0 mg. |

[1]Complexing agent: sodium salt of ethylenediaminetetraacetic acid.

I claim:

1. A method of prophylaxis against the development of epithelial carcinomas of the skin, gastrointestinal tract, respiratory tract or genito-urinary tract which comprises enterally administering to persons susceptible to such carcinomas a composition comprising a medicinally inert, pharmaceutically acceptable carrier material and 13-cis vitamin A acid or a pharmaceutically acceptable salt thereof, said composition being administered in an amount sufficient to provide from about 0.05 mg to about 3.0 mg of 13-cis vitamin A acid or its pharmaceutically acceptable salt per kg of body weight per day.

2. A method in accordance with claim 1 wherein said composition additionally contains an antioxidant selected from the group consisting of alpha-tocopherol, N-methyl-γ-tocopherolamine, butylated hydroxyanisole, butylated hydroxytoluene, ethoxyquin and mixtures thereof.

3. The method in accordance with claim 1 wherein the daily amount of 13-cis vitamin A acid administered is from 0.1 mg. to about 1.0 mg. per kilogram of body weight of said person.

4. A method in accordance with claim 1 wherein said composition is administered in the form of pharmaceutical unit dosage, each unit dosage containing from about 5.0 mg. to about 50.0 mg. of 13-cis vitamin A acid or its pharmaceutically acceptable salt.

5. A method in accordance with claim 1 wherein said pharmaceutically acceptable salt is the sodium salt.

6. A method in accordance with claim 1 wherein said carcinomas are those of the skin, bronchi, gastrointestinal tract, genitalia or oral cavity.

7. A method in accordance with claim 6 wherein said composition is administered in the form of pharmaceutical unit dosage, each unit dosage containing from about 5.0 mg. to about 50.0 mg. of 13-cis vitamin A acid or its pharmaceutically acceptable salt.

8. A method in accordance with claim 6 wherein said composition is administered to patients afflicted with a premalignant condition characterized by a propensity to mature into one of said carcinomas.

9. A method in accordance with claim 8 wherein said premalignant condition is bronchogenic disease.

10. A composition in unit dosage form for enteral administration comprising as an active ingredient 13-cis Vitamin A acid or pharmaceutically acceptable salts thereof and a pharmaceutically acceptable carrier suitable for enteral administration, said active ingredient being present in said composition in an amount of from about 5 mg to about 50 mg.

11. The composition of claim 10 wherein said carrier is vegetable oil.

12. The composition of claim 10 wherein said unit dosage form is a tablet, capsule or dragee.

13. The composition of claim 12 wherein said unit dosage form is a capsule.

* * * * *